US00PP09495P

United States Patent [19]

Bradford et al.

[11] Patent Number: Plant 9,495

[45] Date of Patent: Apr. 2, 1996

[54] NECTARINE TREE 'DIAMOND BRIGHT'

[76] Inventors: Lowell G. Bradford, 12439 E. Savana Rd.; Norman G. Bradford, 11875 E. Savana Rd., both of Le Grand, Calif. 95333

[21] Appl. No.: 408,542

[22] Filed: Mar. 22, 1995

[51] Int. Cl.[6] ..... A01H 5/00

[52] U.S. Cl. ..... Plt./41.1

[58] Field of Search ..... Plt./41.1

[56] References Cited

U.S. PATENT DOCUMENTS

P.P. 4,792 11/1981 Anderson ..... Plt./41.1
P.P. 6,363 11/1988 Bradford et al. ..... Plt./41.1
P.P. 7,507 4/1991 Bradford et al. ..... Plt./41.1

*Primary Examiner*—James R. Feyrer

[57] ABSTRACT

The present invention relates to a nectarine tree and more particularly to a new and distinct variety broadly characterized by a large size, vigorous, hardy, productive and regular bearing tree. The fruit matures under the ecological conditions described approximately the second week in June, with first picking on Jun. 7, 1994. The fruit is uniformly large in size, excellent in flavor, attractively globose in shape, clingstone in type, very firm in texture, and full red in skin color. The variety was developed as a first generation hybridization using August Red Nectarine (U.S. Plant Pat. No. 6,363) as the selected seed parent and Aurora Grand Nectarine (U.S. Plant Pat. No. 4,792) as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Diamond Bright". The present variety was hybridized in 1987 by us in a cultivated area of our experimental orchard at Bradford Farms near Le Grand, Calif. in Merced County (San Joaquin Valley). It was the result of a first generation cross using August Red Nectarine (U.S. Plant Pat. No. 6,363) as the selected seed parent and Aurora Grand Nectarine (U.S. Plant Pat. No. 4,792) as the selected pollen parent. Subsequent to origination of the present variety of nectarine tree, we asexually reproduced it by budding and grafting, and such reproduction of plant and fruit characteristics were true to the original plant in all respects.

The present variety is most similar to the Spring Bright Nectarine (U.S. Plant Pat. No. 7,507) by producing fruit that is large in size, very firm in texture, clingstone in type, and full red in skin color, but is distinguished therefrom and an improvement thereon by blooming 1 week later, having reinform instead of globose glands, having a bitter kernal instead of sweet, and producing fruit that matures 12 days earlier.

The present variety is similar to its seed parent, the August Red (U.S. Plant Pat. No. 6,363), by producing clingstone fruit that is large in size, excellent in flavor, and very firm in texture, but is very distinguished therefrom by producing fruit that matures about 77 days earlier.

The present variety is similar to its pollen parent, the Aurora Grand (U.S. Plant Pat. No. 4,792), in fruit appearance by being a full red colored nectarine with excellent firmness, but is very distinguished therefrom by having a large blossom, instead of small, and by producing fruit that is clingstone instead of freestone, that is larger in size, and that ripens approximately 10 days later.

DRAWING

The accompanying photograph exhibits three whole fruits positioned to display the characteristics of the skin color and form, a sectioned half fruit divided transverse to the suture plane to reveal the flesh, a typical stone, and representative leaves.

POMOLOGICAL CHARACTERISTICS

Referring now more specifically to the pomological characteristics of this new and distinct variety of nectarine tree, the following has been observed under the ecological conditions prevailing near La Grand, Merced County (San Joaquin Valley), Calif., and was developed at the state of hard eating ripe on Jun. 10, 1994. All major color code designations are by reference to the Inter-Society Color Council, National Bureau of Standards. Common color names are also used occasionally.

TREE

Size: Large.
Vigor: Vigorous.
Growth: Spreading and dense.
Form: Round topped.
Hardiness: Hardy.
Production: Productive.
Bearing: Regular bearer.
Trunk:
- *Size.*—Medium.
- *Texture.*—Medium.
- *Bark color.*—Dark brown [59. d.Br].
- *Lenticels.*—Numerous. Color: Moderate yellowish brown [77. m.yBr]. Average size: ⅛" to ⅜" [3.2–9.5 mm.].

Branches:
- *Size.*—Medium.
- *Texture.*—Medium.
- *Color.*—1st Year Wood Topside: Dark red [16. d.R]. 1st Year Wood Underside: Moderate yellow green [120. m.YG]. Older Wood: Moderate brown [58. m.Br].
- *Lenticels.*—Numerous, very small. Color: Light yellowish brown [76. l.yBr]. Average size: 1/16" [1.6 mm.].

Leaves:
- *Size.*—Medium. Average length: 5¼" [133.4 mm.]. Average width: 1 7/16" [36.5 mm.].

*Thickness.*—Medium.
*Form.*—Elliptical.
*Apex.*—Acuminate.
*Base.*—Acute.
*Surface.*—Smooth.
*Color.*—Dorsal surface: Moderate olive green [125. m.OlG]. Ventral surface: Moderate yellow green [120. m.YG].
*Margin.*—Finely serrate.
*Venation.*—Pinnately net veined.
*Petiole.*—Average length: 7/16" [11.1 mm.]. Average thickness: 1/16" [1.6 mm.]. Dorsal color: Brilliant yellow green [116. brill.YG]. Ventral color: Brilliant yellow green [116. brill.YG].
*Stipules.*—Moderate in number. Average length: 1/4" [6.4 mm.].
*Glands.*—Average number: 2–4 per leaf. Position: Usually oppositely, but occasionally alternately, positioned on petiole and base of blade, with a few singles. Size: Small. Form: Reniform. Color: Grayish red [19. gy.R].

Flower buds:
*Hardiness.*—Hardy.
*Size.—Medium.*
*Length.—Medium.*
*Form.*—Free.
*Surface.*—Pubescent.

Flowers:
*Blooming period.*—Late as compared with other varieties.
*Size.*—Large.
*Color.*—Light purplish pink [249. l.Pk].

FRUIT

Maturity when described: Hard ripe, Jun. 10, 1994.
Date of first picking: Jun. 7, 1994.
Date of last picking: Jun. 18, 1994.
Size: Uniform, medium.
*Average diameter axially.*—2½" [63.5 mm.].
*Average transversely in suture plane.*—2⅝" [66.7 mm.].
Form: Uniform, globose.
*Longitudinal section form.*—Round, but truncate at base.
*Transverse section through diameter.*—Round.
Suture: An inconspicuous line becoming a shallow groove towards the apex, extending from the base to just beyond the apex, with a slight depression beyond the pistil point.
Ventral surface: Rounded, lipped toward the apex on both sides.
Lips: Equal.
Cavity: Flaring, circular, suture showing on one side.
*Depth.*—⅜" [9.5 mm.].
*Breadth.*—⅝" [15.9 mm.].
Base: Rounded, truncate.
Apex: Uniform.
Pistil point: Apical, negligible in length, depressed within the suture.
Stem: Medium.
*Average length.*—⅜" [9.5 mm.].
*Average width.*—3/16" [4.8 mm.].
Skin:
*Thickness.*—Medium.
*Texture.*—Medium.
*Tenacity.*—Tenacious to flesh.
*Tendency to crack.*—None observed.
*Color.*—Very dark red [17. v.d.R] with deep red [13. deep R] background and slight moderate orange yellow [71. m.OY] freckling near the apex.

Flesh:
*Color.*—Light orange yellow [70. l.OY] virtually to pit with only very slight strong red [1.2 s.R] streaking close to the stone.
*Amygdalin.*—Moderate.
*Juice.*—Abundant, rich.
*Texture.*—Very firm, fine, crisp.
*Fibers.*—Abundant, fine, tender.
*Ripens.*—Evenly.
*Flavor.*—Very delicious blend of acid and sugar with 15 to 17 brix.
*Aroma.*—Moderate.
*Eating quality.*—Best.

STONE

Type: Clingstone.
Form: Oblong to elliptical.
Base: Straight.
Apex: Acute.
Sides: Equal.
Surface: Furrowed toward the apex and pitted toward the base.
Ridges: Horizontal near the apex, jagged toward the base.
Color: Pale orange yellow [73. p.OY] when dry.
Pit wall: 3/16" [4.8 mm.] thick.
Tendency to split: Slight.
Kernel:
*Form.*—Oval.
*Taste.*—Bitter.
*Viable.*—Only with embryo culture.
*Average width.*—½" [12.7 mm.].
*Average length.*—¾" [19.1 mm.].
*Color.*—Pale yellow [89. p.Y] when first cracked, strong yellowish brown [74. s.yBr] when dry.
*Pellicle color.*—Light grayish yellowish brown [79. l.gy.yBr].
*Amygdalin.*—Moderate.

USE

Market: Fresh and long distance shipping.
Keeping quality: Excellent.
Shipping qualtiy: Excellent.
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, which is most similar to the Spring Bright Nectarine (U.S. Plant Pat. No. 7,507) by producing fruit that is large in size, very firm in texture, clingstone in type, and full red in skin color, but is distinguished therefrom and an improvement thereon by blooming 1 week later, by having reniform instead of globose glands, by having a bitter kernel instead of sweet, and by producing fruit that matures 12 days earlier.

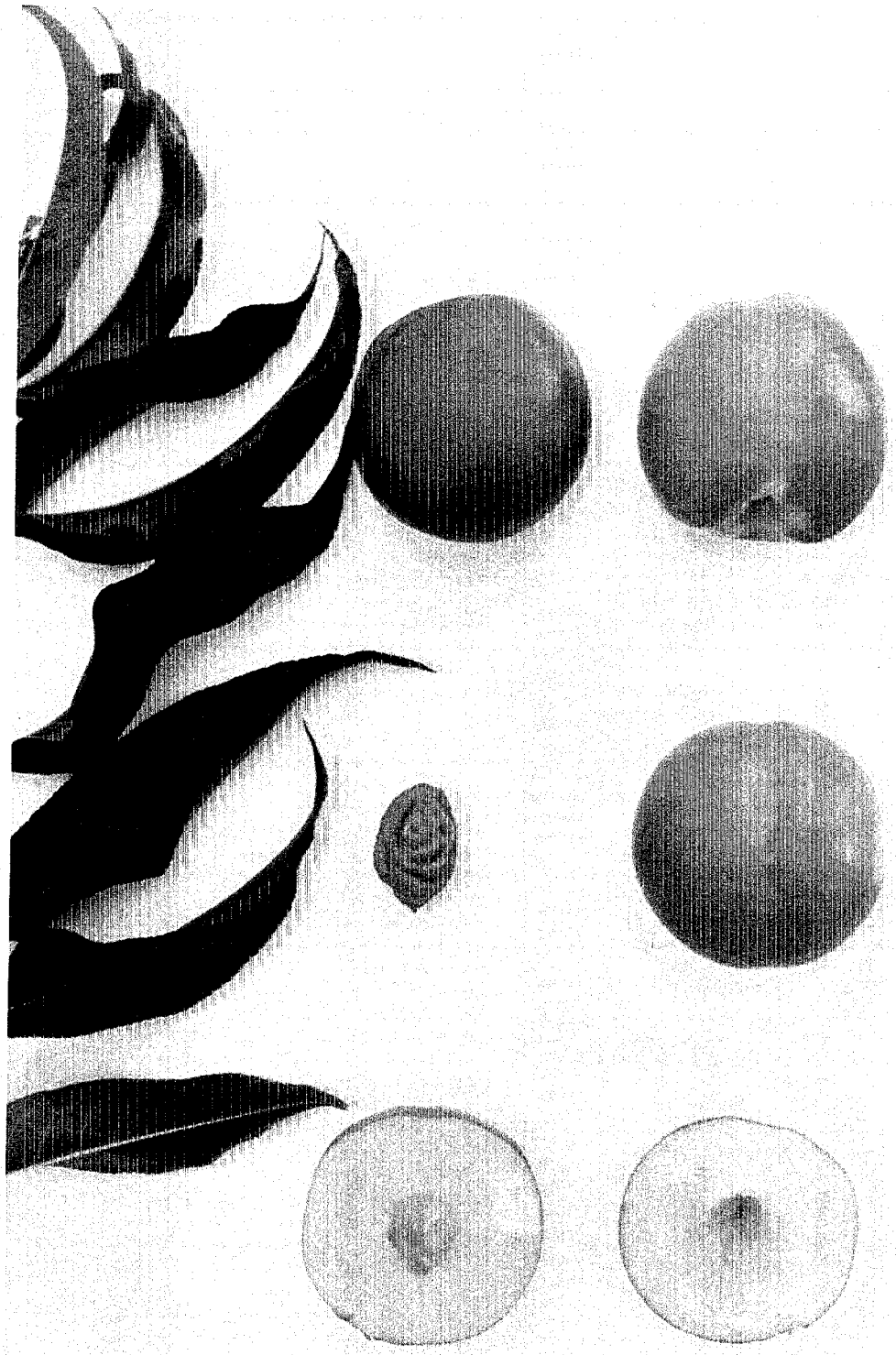

* * * * *